(12) United States Patent
McGuinness et al.

(10) Patent No.: US 11,486,839 B2
(45) Date of Patent: Nov. 1, 2022

(54) DIAGNOSTIC CASSETTE

(71) Applicant: Hewlett-Packard Development Company, L.P., Houston, TX (US)

(72) Inventors: Nicholas Matthew Cooper McGuinness, San Diego, CA (US); Manish Giri, Corvallis, OR (US); Chantelle Elizabeth Domingue, Corvallis, OR (US); Melinda M. Valencia, Chula Vista, CA (US); Jeremy Sells, Albany, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 833 days.

(21) Appl. No.: 15/300,698

(22) PCT Filed: Apr. 25, 2014

(86) PCT No.: PCT/US2014/035534
§ 371 (c)(1),
(2) Date: Sep. 29, 2016

(87) PCT Pub. No.: WO2015/163921
PCT Pub. Date: Oct. 29, 2015

(65) Prior Publication Data
US 2017/0108455 A1    Apr. 20, 2017

(51) Int. Cl.
*G01N 27/02* (2006.01)
*B01L 3/00* (2006.01)
(Continued)

(52) U.S. Cl.
CPC ........... *G01N 27/02* (2013.01); *A61B 5/1477* (2013.01); *A61B 5/14507* (2013.01);
(Continued)

(58) Field of Classification Search
CPC .. G01N 27/02; A61B 5/1477; A61B 5/14507; A61B 5/14546; A61B 2503/42;
(Continued)

(56) References Cited

U.S. PATENT DOCUMENTS 5,836,750 A * 11/1998 Cabuz ............... A61M 5/14224
                                                417/322
2002/0005354 A1 * 1/2002 Spence ............. B01L 3/502761
                                                204/450

(Continued)

FOREIGN PATENT DOCUMENTS

JP    H11-500602    1/1999
JP    2005-283331   10/2005
(Continued)

OTHER PUBLICATIONS

Chin, C.D. et al.; Low-cost Microdevices for Point-of-care Testing; Springer-Verlag Berlin Heidelberg; Oct. 13, 2013; pp. 3-22.
(Continued)

*Primary Examiner* — Dennis White
(74) *Attorney, Agent, or Firm* — Fabian VanCott (57) ABSTRACT

A diagnostic cassette includes a substrate, to physically and electrically connect the product to a computing device, a reservoir defined within the substrate to receive a fluid sample for processing by the diagnostic cassette, a reagent to react with the fluid sample deposited in the reservoir to form a solution to enable processing of the fluid sample by the diagnostic cassette, a channel to direct the solution, and a sensor to measure a number of parameters of the solution passing through the channel. A method for measuring microfluidic samples includes receiving, in a reservoir, a fluid sample to be measured, combining the fluid sample with a reagent to create a solution, moving the solution through a
(Continued)

channel, and measuring the solution, using sensors, as the solution passes through the channel.

2 Claims, 8 Drawing Sheets

(51) Int. Cl.
 *A61B 5/145* (2006.01)
 *A61B 5/1477* (2006.01)
 *A61B 5/00* (2006.01)

(52) U.S. Cl.
 CPC .... *A61B 5/14546* (2013.01); *B01L 3/502715* (2013.01); *A61B 5/41* (2013.01); *A61B 2503/42* (2013.01); *A61B 2560/0456* (2013.01); *A61B 2560/0462* (2013.01); *A61B 2562/028* (2013.01); *B01L 3/502761* (2013.01); *B01L 2200/0652* (2013.01); *B01L 2200/16* (2013.01); *B01L 2300/0645* (2013.01); *B01L 2300/0816* (2013.01); *B01L 2300/0867* (2013.01); *B01L 2400/0487* (2013.01)

(58) Field of Classification Search
 CPC .... A61B 2560/0456; A61B 2560/0462; A61B 2562/028; A61B 5/41; B01L 3/502715; B01L 2200/0652; B01L 3/502761; B01L 2300/0867; B01L 2300/0816; B01L 2300/0645; B01L 2200/16; B01L 2400/0487
 See application file for complete search history.

(56) References Cited

U.S. PATENT DOCUMENTS

| | | | |
|---|---|---|---|
| 2003/0148530 A1 | 8/2003 | Lauks | |
| 2003/0175947 A1* | 9/2003 | Liu | B01F 11/0071 435/288.5 |
| 2005/0255001 A1* | 11/2005 | Padmanabhan | G01N 15/1404 422/73 |
| 2007/0154895 A1 | 7/2007 | Spaid et al. | |
| 2008/0221805 A1 | 9/2008 | Andrews | |
| 2009/0185955 A1 | 7/2009 | Nellissen et al. | |
| 2011/0253222 A1 | 10/2011 | Arai | |
| 2011/0275111 A1 | 11/2011 | Pettigrew et al. | |
| 2011/0279130 A1 | 11/2011 | Reccius et al. | |
| 2011/0308313 A1* | 12/2011 | Azimi | B01L 3/5027 73/335.04 |
| 2012/0129716 A1* | 5/2012 | Chee | B01L 3/502761 506/9 |
| 2013/0085680 A1 | 4/2013 | Arlen et al. | |

FOREIGN PATENT DOCUMENTS

| | | |
|---|---|---|
| JP | 2008-519978 | 6/2008 |
| JP | 2009236933 | 10/2009 |
| JP | 2011-122858 | 6/2011 |
| JP | 2011-203272 | 10/2011 |
| JP | 2013533102 | 8/2013 |
| JP | 2014-029327 | 2/2014 |
| WO | WO-9933559 A1 | 7/1999 |
| WO | WO-2004061418 | 7/2004 |
| WO | WO-2008101196 A1 | 8/2008 |
| WO | WO-2012064878 | 5/2012 |
| WO | WO-2012096480 | 7/2012 |
| WO | WO-2012110922 | 8/2012 |
| WO | WO-2013117233 | 8/2013 |
| WO | WO-2014046687 A1 | 3/2014 |

OTHER PUBLICATIONS

Chen et al., 'An integrated, self-contained microfluidic cassette for isolation, amplification, and detection of nucleic acids' Biomedical Microdevices, vol. 12. Issue 4, pp. 705-719 (2010).

Kruger et al., 'Development of a microfluidic device for fluorescence activated cell sorting' Journal of Micromechanics and Microengineering, vol. 12, No. 4, pp. 486-494 (2002).

Lee et al., 'Nano/Microfluidics for diagnosis of infectious diseases in developing countries' Advanced Drug Delivery Reviews, vol. 62, Issues 4-5, pp. 449-457 (2010).

* cited by examiner

DIAGNOSTIC CASSETTE

BACKGROUND

Diagnostic equipment systems and methods for testing fluid samples, such as those used for detecting human immunodeficiency virus (HIV), have a wide range of complexities. Some devices and methods use refrigeration, reagents, a microscope, a hemocytometer, calibrated pipettes, and test tubes. Further, a trained technician prepares samples and manually counts results.

Another method for testing fluid samples is flow cytometry, which uses fluorescence-activated cell sorting. In this example, samples are prepared with antibodies that fluorescently label the cells. Samples are incubated before they are ready for analysis. Once in the system, samples are passed through an excitation laser beam. The scattered light from the cells passing through the beam is collected, filtered, and converted to an electrical signal. The samples are also amplified, digitized, and stored for analysis. Methods such as hydrodynamic focusing, referred to as sheath flow, and acoustics are used to ensure cells pass through the beam one at a time.

Portable cytometers use similar technology. In this example, the sample is taken and mixed with reagents that fluorescently label specific cells. The sample is passed through a laser beam, and the amount of light scattered is collected and converted to an electric signal that can be used to measure the number of labeled cells in the sample.

BRIEF DESCRIPTION OF THE DRAWINGS

The accompanying drawings illustrate various examples of the principles described herein and are a part of the specification. The examples do not limit the scope of the claims.

Throughout the drawings, identical reference numbers designate similar, but not necessarily identical, elements.

DETAILED DESCRIPTION

Complex and expensive healthcare diagnostic equipment may be cost- and staffing-prohibitive to many medical service providers. This diagnostic equipment is often deployed in hospitals and laboratories that have sufficient budget and staff. Remote areas may not have access to hospitals or laboratories with this equipment. The separation of service and diagnostic equipment may increase costs, or prevent tests from being run. By providing simplified, accurate diagnostic testing at the point of care, access to this testing may be expanded to remote areas.

Some point-of-care diagnostic testing solutions prepare a sample prior to using diagnostic equipment. This preparation may mix a fluid sample with a reagent and incubate the solution for a period of time. The reagent may fluorescently mark cells that are to be detected by the diagnostic device. A device of this nature may further use some form of external force, such as pumping, to move the cells through a device so the cells can be measured.

A living cell is the basic structural and functional unit of an organism. Most animal and plant cells range in size from 1-100 μm and contain vital heath information. Cell based diagnostics is the gold standard for detecting infectious diseases such as HIV, malaria, and tuberculosis. Cell based diagnostics is also the standard for chronic diseases such as cancer, cardiac conditions, and autoimmune deficiency syndrome.

The ability to receive a sample, create a solution of the sample and a reagent, move the solution through channels and past sensors, and read measurements from sensors may be integrated onto a single device. The device may be constructed for a single use, or may be constructed for multiple uses. The device may be connected to a computing device, such as a personal computer, laptop, tablet, smart phone, or other similar devices. The computing device may be used to control components of the diagnostic device, and/or to control measurement rates of a sample. The computing device may also be used to read and display measurements taken from the sensors on the diagnostic device.

The present systems and methods describe a device comprising a substrate used to physically and electrically connect the product to a computer device. A reservoir may be mounted to the substrate to receive fluid samples to be measured by the device. In one example, a second reservoir may be used to receive a reagent to react with the fluid sample to enable measurement of the sample. In another example, the same reservoir may receive both a fluid sample and a reagent. In a different example the reservoir may receive a fluid sample, while other portions of the device may contain a reagent to add to the fluid sample.

The reagent may perform a variety of functions to enable processing of the fluid sample. For example, a reagent may include a compound that reacts with elements of the fluid sample. In this example, the device measures attributes of the reaction. A reagent may contain compounds to prevent natural reactions in the fluid sample. For example, the reagent may contain an anti-coagulant to prevent coagulation prior to measurement of the sample. A reagent may also serve to dilute the fluid sample in order to permit more accurate measurement of particles in the fluid sample. A number of reagents may be applied to a number of different areas of the device to permit measurements of a number of attributes of the fluid sample.

Several microfluidic and impedance-sensing designs adapting thermal inkjet resistors and impendence sensors may be included within the present system to allow for effective measurement of microfluidic samples. The thermal inkjet resistors are used to circulate fluids and particles in microfluidic channels.

Microstructures, such as channels, may be used to direct cells of different sizes to different areas of the device, allowing for separation and filtration of particles. The microstructures may be used to influence diffusion between the fluid sample and the reagent by influencing the intimate contact between them. The microstructures may also be formed to influence the movement of the solution of the fluid sample and the reagent in order to allow for reaction time between the fluid sample and the reagent.

Impedance sensing circuits can detect fluid types and count cells using impedance signatures. Frequency sweeps of an in-channel micro impedance sensor characterize a unique response for different fluids. At a constant frequency, the impedance response detected while cells pass over the sensor can provide information about the health, type, and size of cells, or combination of these and other attributes. A pump, such as a thermal inkjet resistor, may be used to circulate fluid samples and ensure movement of cells over impedance sensors. Depending on the implementation, after the cells have passed the sensors, they may be sorted and re-measured, dispensed, continuously circulated, or allowed to accumulate in a reservoir.

Sensors may be used to measure other attributes of the fluid sample based on the nature of the fluid sample, reagent, and the property being stated. For example, the present systems may measure the impedance of cells in a solution of the sample. A different example may measure inductive attributes of cells. Another example may count cells based on the size of the cells. Any number of attributes for which sensors are created may be used by the device to measure attributes of the fluid sample.

Methods of controlling a device constructed according to the principles described herein are also described herein. A method may comprise receiving a fluid sample into the reservoir of the device. The fluid sample may then be combined with a reagent to create a solution for processing. The solution is then moved through a channel past a sensor. The sensor measures attributes of the solution or cells in the solution as they pass the sensor. The solution may be moved using pressure on the fluid, or may be moved using suction.

A computing device may measure parameters of a sample. The computing device comprises a module that pumps a sample from a reservoir to initiate a diagnostic process. A different module controls diffusion between a fluid sample and a reagent to facilitate the diagnostic process. Another module reads measurements from a sensor, which measures attributes of the solution. Based on the measurements from the sensor, another module calculates a result.

The computing device may include a module that controls a sorting of elements within the fluid sample. The computer product may also include code to manipulate a device to further process the sorted elements to obtain more information.

As used in the present specification and in the appended claims, the term "a number of" or similar language may include any positive number including one to infinity; zero not being a number, but the absence of a number.

In the following description, for purposes of explanation, numerous specific details are set forth in order to provide a thorough understanding of the present systems and methods. It will be apparent, however, to one skilled in the art, that the present apparatus, systems, and methods may be practiced without these specific details. Reference in the specification to "an example" or similar language means that a particular feature, structure, or characteristic described in connection with that example is included as described, but may not be included in other examples.

Figure 1:
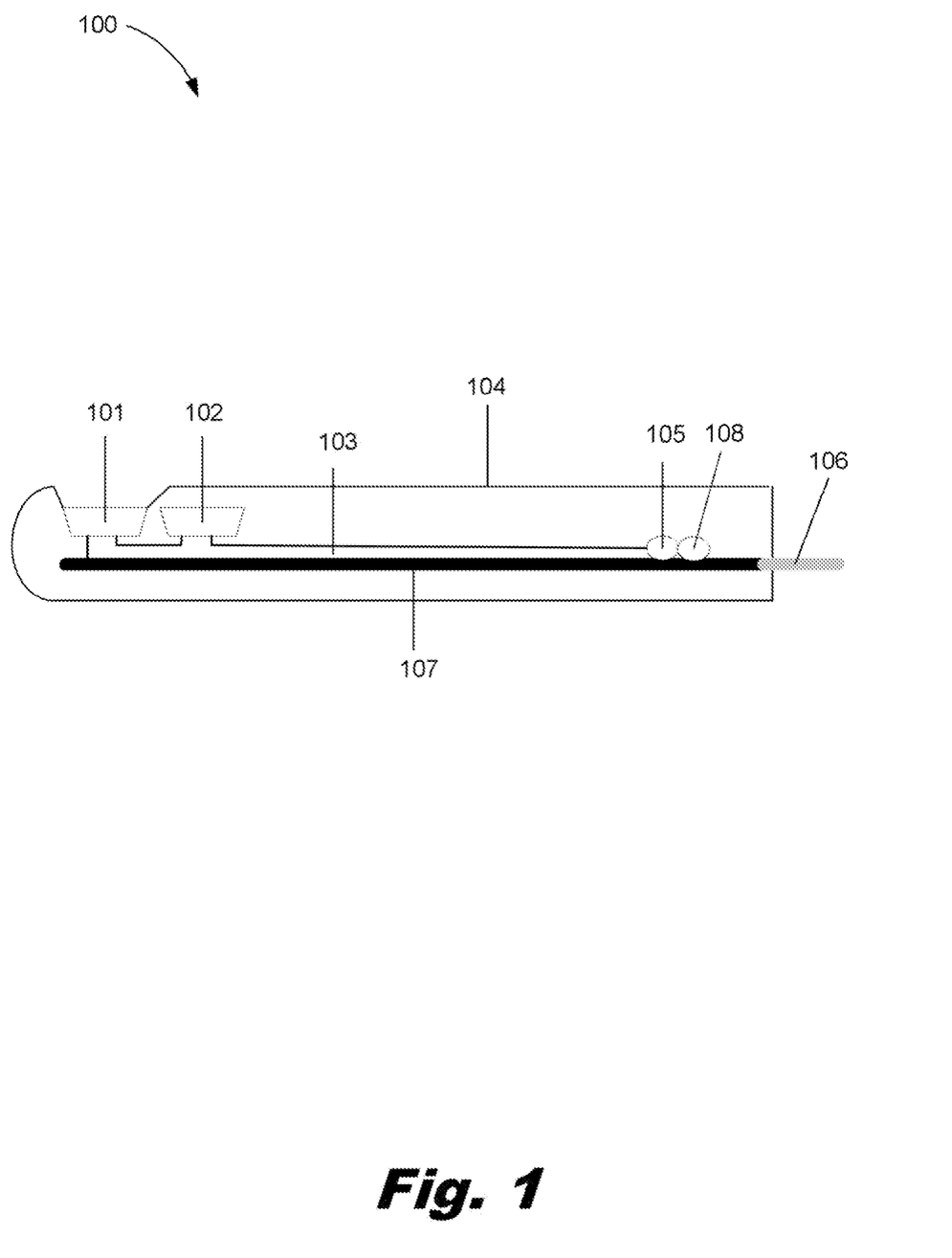
FIG. 1 is a cross sectional diagram of an apparatus for testing fluid samples, according to one example of the principles described herein.

Referring now to the figures, FIG. 1 is a diagram of an example of a diagnostic cassette (100) according to one example of the principles described herein. As will be described, the diagnostic cassette (100) may include a number of sample reservoirs (101) to receive a sample, a number of reagent reservoirs (102), a number of micro-channels (103), a number of sensors (105), a number of pumps (108), a substrate (107), a computer port (106), and a housing (104).

The sample reservoir (101) may receive the sample into the diagnostic cassette (100) for processing. The sample may be received directly from a subject being diagnosed, or may be received as a portion of a larger sample. The sample reservoir (101) may include a mechanism, such as a needle or lance, to extract a sample from a subject. The sample reservoir may be left exposed, or may include a covering for storage before and/or after the sample is obtained.

The reagent reservoir (102) may be separate from the sample reservoir (101). The diagnostic cassette (100) may be manufactured with a reagent present in the reagent reservoir (102). The reagent may take the form of a liquid, or may be a powder or other substance. The reagent reservoir (102) may be eliminated and the reagent may be applied to the sample in the sample reservoir (101).

The reagent reservoir (102) may hold the reagent separate from the fluid sample to control at what time and rate the diffusion of the fluid sample and reagent are to occur. In one example, the reagent and the fluid sample may be combined prior to receiving the sample in the sample reservoir (101).

The micro-channel (103) connects to the sample reservoir (101) to allow for the removal of the fluid sample into the diagnostic process. The removal of the fluid sample from the sample reservoir (101) into the micro-channel (103) may occur through suction created by, for example, a pump (108) located in fluid communication with the micro-channel (103).

The micro-channel (103) may also connect to the reagent reservoir (102) to allow for the removal of the reagent from the reagent reservoir. The fluid sample and reagent may be combined either in the sample reservoir (101), the reagent reservoir (102), another reservoir, or the micro-channel (103).

The micro-channel (103) may be formed to influence the rate of contact between the fluid sample and the reagent. Reaction between the fluid sample and reagent may be used to create substances in the solution, or to allow cells in the fluid sample to react with substances in the reagent. The micro-channel (103) may be formed to enhance or inhibit the contact between the fluid sample and the reagent to influence the rate and time of diffusion between the substances. An increase in the diffusion between the fluid sample and the reagent may increase the reaction between the substances, which may enhance the ability of the diagnostic cassette (100) to obtain accurate measurements.

The micro-channel (103) may also be formed to alter the rate of diffusion between the fluid sample and the reagent. For instance, a relatively large, straight micro-channel (103) may not observe the same rate of diffusion as a smaller micro-channel (103) that is designed with frequent changes of shape to enhance diffusion. The size of the micro-channel (103) itself may encourage diffusion, and/or changes in the micro-channel (103) may cause particles and cells in the solution to diffuse at a different rate.

The micro-channel (103) may be formed and the length may be constructed to modify the amount of time the fluid sample and the reagent are in contact prior to being measured by the sensor (105). The shape and length of the micro-channel may vary between devices, depending on the application, in order to vary the amount of reaction time the fluid sample and reagent may have. A reaction time that is too brief may result in the correct substances not being measurable or measured when the solution passes the sensor (105). A reaction time that is too long may result in a measurable decay in substances when the solution passes the sensor (105).

A diagnostic cassette (100) may have one sensor (105) or may have multiple sensors (105) to measure substances in the solution of the fluid sample and the reagent. A sensor (105) may measure the impedance of cells in the solution. The cells' impedance signature may be altered by a reaction between the cell and the reagent. A reagent may enhance or alter the impedance signature of a cell to make it easier to measure, or to make it easier to distinguish different types of cells that would naturally have a similar impedance signature.

A sensor (105) may test properties of the solution aside from or in addition to impedance. For instance, a sensor (105) may detect the size, mass, density or other of a cell. A series of sensors (105) may be used to sort cells in the solution on the basis of multiple attributes. For example, cells may be sorted and counted such that cells with a particular range of impedance and size are reported, while other cells that do not share those properties are not reported. The sensor (105) may include an integrated computer chip or chips to process and communicate measurements from the sensor (105). The integrated computer chip or chips may process the signal and perform calculations, or may directly report the signal through the computer port (106).

Different sensors (105) may be included in a single diagnostic cartridge (100). Different diagnostic cartridges (100) may be manufactured to detect different properties in respective fluid samples by including different types of sensors (105).

A substrate (107) may physically and mechanically connect the fluid sample reservoir (101), the reagent reservoir (102), and the sensor (105) to a computer port (106). The substrate (107) may include electrical wiring to connect the sensor (105) and the computer port (106). The computer port (106) may send and receive electrical signals between a computing device and the sensor (105). The substrate (107) may carry electrical signals between a pump (108) and the computer port (106), allowing for control of and measurements from the pump (108).

The substrate (107) may include multiple layers to perform various functions. For instance, a substrate (107) may include three layers to form the micro-channel (103). The first substrate (107) layer may form the bottom of the micro-channel (103), and a second layer of substrate (107) may form the walls of the micro-channel (103). A third layer of substrate may form the top of the micro-channel (103). Additionally, combinations of the substrate may form various components of the micro-channel (103), the fluid sample reservoir (101) and the reagent reservoir (102).

The computer port (106) may connect the diagnostic cartridge (100) to a computing device. The computing device may read measurements from the sensors (105) on the diagnostic device (100). The computing device may also program sensors (105) or pumps (108) to control the rate of reaction and measurement in the diagnostic device (100).

The computer port (106) may be an interface such as a Universal Serial Bus (USB), a mini-USB, a micro-USB, or any other interface that provides connectivity between the diagnostic cassette (100) and the computing device. The computer port (106) may provide a wired interface comprising, for example, a cable to separate the diagnostic cassette (100) from the computing device. The computer port (106) may also provide a wireless, non-physical connectivity between the diagnostic cartridge (100) and the computing device, such as connectivity through radio waves. In this example of wireless communication between the diagnostic cartridge (100) and the computing device, a number of transceivers may be located within the diagnostic cartridge (100) and the computing device to send and receive data wirelessly.

The diagnostic cassette (100) may be encompassed by a housing (104). The housing (104) may provide protection of internal components such as the sensors (105). The housing (104) may form a part or all of the fluid sample reservoir (101), the reagent reservoir (102), or a combination thereof. The housing (100) may be formed to accommodate the substrate (107) and other components. Additionally, the housing (104) may be formed so as to show a visible and tangible difference between diagnostic cassettes (100) built for different types of diagnostic testing.

The housing (104) may be formed for aesthetic reasons. The housing (104) may be formed so as to enhance the handling of the diagnostic cassette (100) by an operator. The shape of the housing (104) may also allow for labelling of the sample, logos, or other information pertaining to the diagnostic cassette.

Figure 2:
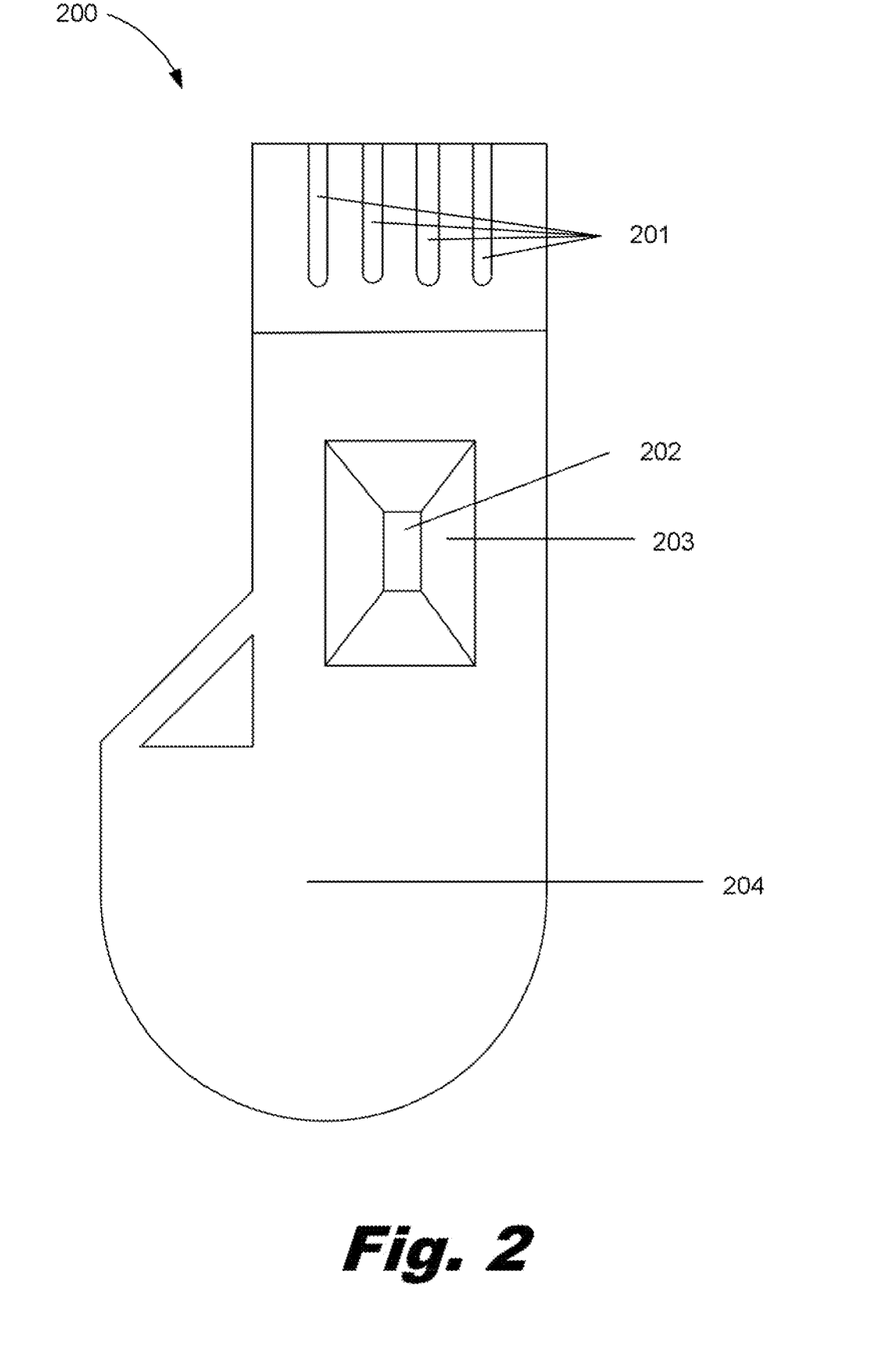
FIG. 2 is a view of the apparatus of FIG. 1, according to one example of the principles described herein.

FIG. 2 is a diagram of an example of a diagnostic cassette (200) according to the principles described herein. The diagnostic cassette (200) may include a connector (201) or series of connectors (201) to a computing device. The connector (201) may be a Universal Serial Bus (USB) port, or similar technology. The connector (201) may include interface components to allow wireless network connectivity such as IEEE 802.11 (Wi-Fi), or a personal area network such as IEEE 802.15.1 (Bluetooth). The connector (201) may be physically and electrically connected to the substrate (FIG. 1, 107).

The diagnostic cassette (200) may be encompassed by a housing (204). The housing (204) may serve to protect components of the diagnostic cassette (200), to allow for labelling of the diagnostic cassette (200), for identification of the diagnostic cassette (200), or similar purposes.

The housing (204) may be shaped to create a feed system (203) to direct a fluid sample toward the fluid sample reservoir (202). The feed system (203) may be manufactured as a single part with the fluid sample reservoir (202). The feed system (203) may also prevent the fluid sample from coming into contact with other components of the diagnostic cassette (200).

Figure 3:
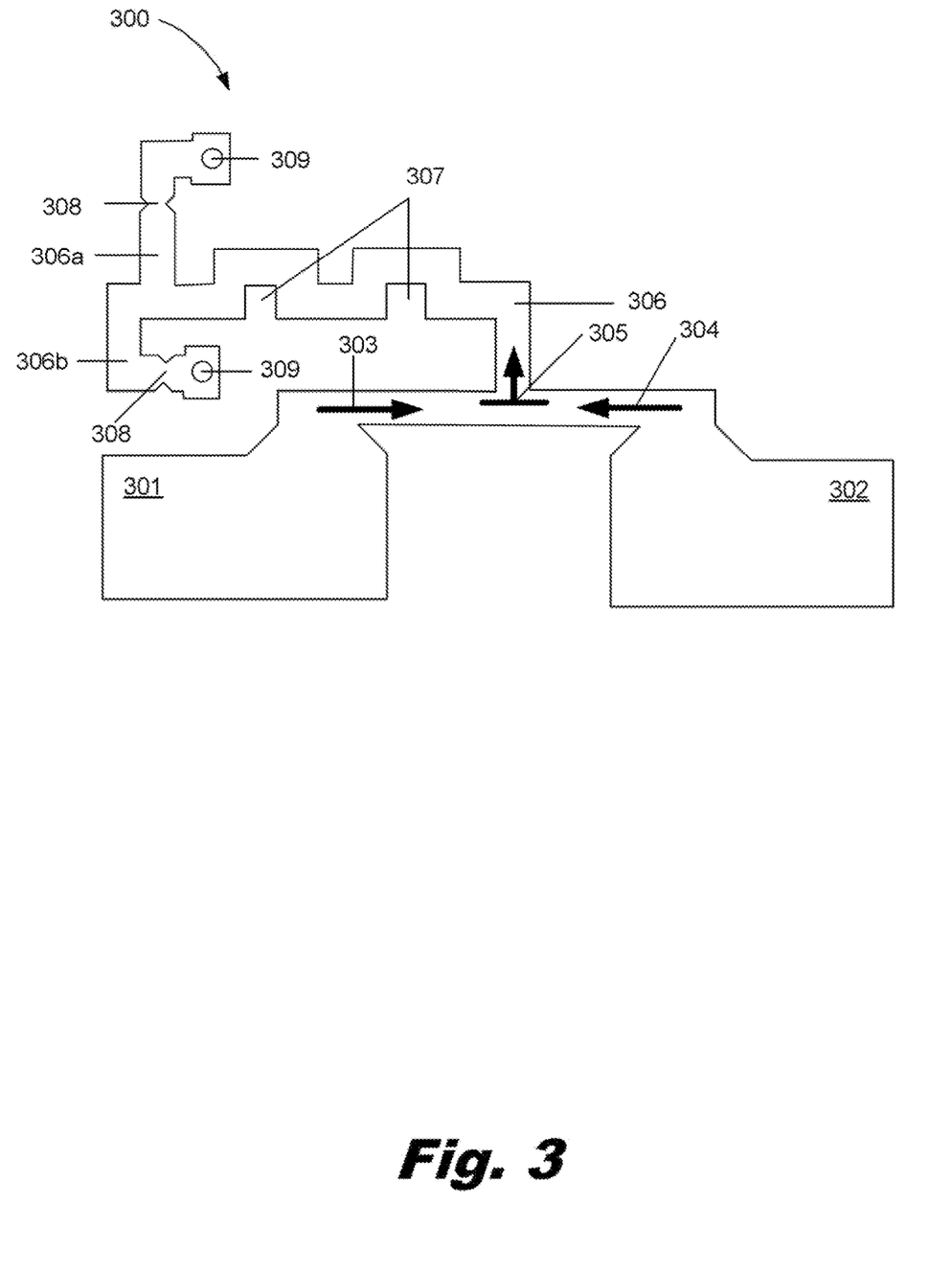
FIG. 3 is a diagram of the apparatus of FIG. 1 with a protective shell removed, according to one example of the principles described herein.

FIG. 3 is a block diagram of a diagnostic cassette (300) for micro-fluidic testing, according to an example of the principles described herein. The diagnostic cassette may include a fluid sample reservoir (301) to receive fluid samples to be processed. The fluid sample reservoir may be fluidly coupled to the feed system (FIG. 2, 203). The fluid sample deposited into the fluid sample reservoir (301) may create a fluid sample flow (303) through a channel (306) by suction created by a pump (309).

Similarly, a reagent may be stored or applied to a reagent reservoir (302). The reagent reservoir (302) may be populated at the time of manufacture, or may be populated closer to the time the diagnostic cassette (300) is used. The reagent may create a reagent flow (304) through a channel (306) by suction created by the pump (309).

The fluid sample flow (303) and reagent flow (304) may come into contact with each other in a channel (306) to create a solution. The solution may then be drawn in a solution flow (305) through the channel (306). The size and shape of the channel (306) may be constructed to affect the rate of diffusion in the solution flow (305). For instance, a smaller channel (306) may cause a greater diffusion rate between the fluid sample and reagent in the solution flow (305). A larger channel (306) may allow for a lower diffusion rate between the fluid sample and the reagent in the solution flow.

Additionally, the channel (306) may be shaped to influence the diffusion and reaction between particles in the solution flow (305). The channel (306) may include microstructures (307) to restrict or impeded the solution flow (305) through the channel (306). The microstructures (307) may lengthen the channel (306) allowing more time for reaction and diffusion within the solution. The microstructures (307) may also cause cells and particles in the solution to alter their path in the solution flow (305), further enhancing the diffusion of the fluid sample and the reagent.

The channel (306) may divide into multiple channels (306a, 306b). A diagnostic cassette (300) may have a number of sensors (308). Multiple channels (306a, 306b) may allow for more sensors (308) to test the solution. The sensors (308) may test for the same properties of the solution, or they may test different properties of the solution. The sensors may be positioned through the channel (306) to test all or a portion of the solution. Further, the sensors (308) may be positioned to run serially, or in parallel.

Redundant sensors (308) may be positioned on a device to allow for the failure of an individual sensor while still allowing the diagnostic cassette (300) to correctly measure properties of the fluid sample. Redundant sensors (308) may also be used to compare measurements, to ameliorate minor variations in measurements. By averaging data obtained from multiple sensors (308) a more accurate measurement may be provided.

A sensor (308) may be connected directly to a computer port (FIG. 2, 201) by circuitry or by a similar method to communicate the between the sensor (308) and a computing device. The sensor (308) may be activated by the computing device. The sensor (308) may also provide communication to the computing device as to the measurement the sensor (308) has observed.

A sensor (308) may be used in combination with other components to sort cells in the solution. The sensor (308) may be used to control mechanical apparatus for sorting of material or cells in the solution. The sensor (308) may be used to control components to move or prevent movement of material or cells in the solution.

A pump (309) may be used within the diagnostic cassette (300) to facilitate the flow of fluids, such as the fluid sample flow (303), the reagent flow (304), the solution flow (305), or a combination thereof. One example of a pump (309) is a device known as a thermal inkjet technology. The pump (309) may create suction by removing fluid from the channel (306). A pump (309) may also be placed at other points in the diagnostic cassette (300) in order to create pressure to move the fluid. For example, a pump (309) creating pressure may be placed in the fluid sample reservoir (301) and/or the reagent reservoir (302). A pump (309) may mechanically move the solution.

Figure 4:
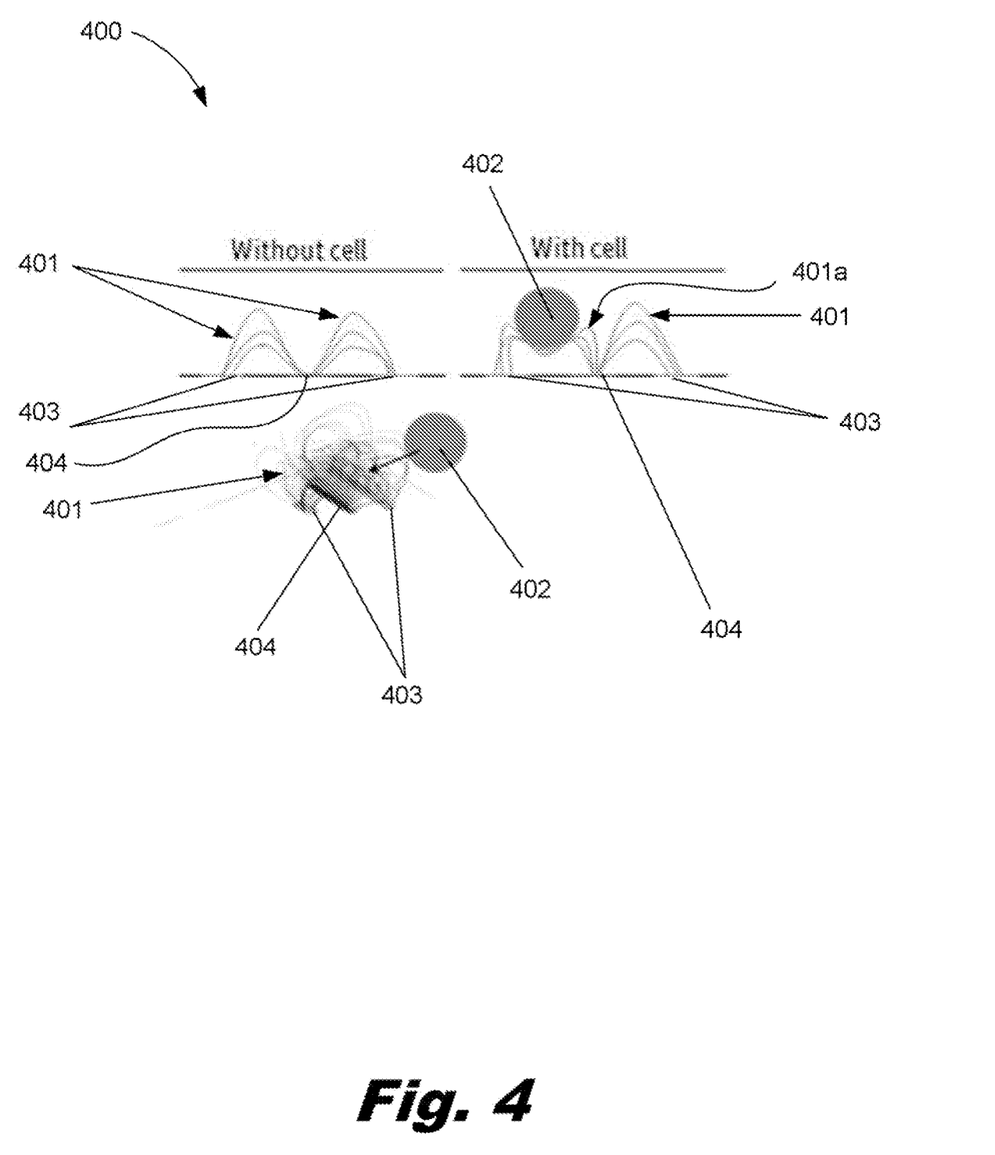
FIG. 4 is an illustration of electric fields experienced within a sensor of the apparatus of FIG. 1, according to one example of the principles described herein.

FIG. 4 is an example of a sensor diagram (400) illustrating a sensor (404) with a cell (402) passing a sensor (FIG. 1, 105) having a sensing electrode (404). Alternative examples of a sensor (FIG. 1, 105) may be used in the diagnostic cassette (FIG. 1, 100). The sensing electrode (404) may detect electrical fields (401) between the sensing electrode (404) and a grounded electrode (403). The sensing electrode (404) may detect variations in the electrical fields (401) to detect attributes of a cell (402) as it passes through the electrical fields (401). The electrical fields (401) may bend or alter based on properties of the cell (402). A varied electrical field (401a) may be detected by the sensing electrode (404). The alteration of the electrical field (401) may indicate particular attributes of the cell (402).

A sensor (FIG. 1, 105) may be constructed to have a single sensing electrode (404) or may be constructed to have multiple sensing electrodes (404). Similarly, a sensor (FIG. 1, 104) may be constructed to have a single grounded electrode (403) or multiple grounded electrodes (403).

The sensing electrode (404) may have an electrical charge which creates an electric field (401) between the sensing electrode (404) and the grounded electrode (403). The electric field (401) may exhibit a steady state, allowing the sensing electrode (404) to detect variations in the electric field (401). For instance, the sensing electrode may detect impedance as a cell (402) passes through the electric field (401), bending the electric field (401a) and causing a variation in the impedance. The sensing electrode (404) may then communicate the variation of impedance to other components of the diagnostic cassette.

The electrical field (401) may be direct, or may vary in any number of directions. Electrical fields (401) may vary in direction, shape, or density. The electrical field (401) may be used to detect impedance, or the resistance of the solution as it passes the sensor (FIG. 1, 105). The localized electric field (401) may be generated by micro-fabricated electrodes (403, 404).

Figure 5:
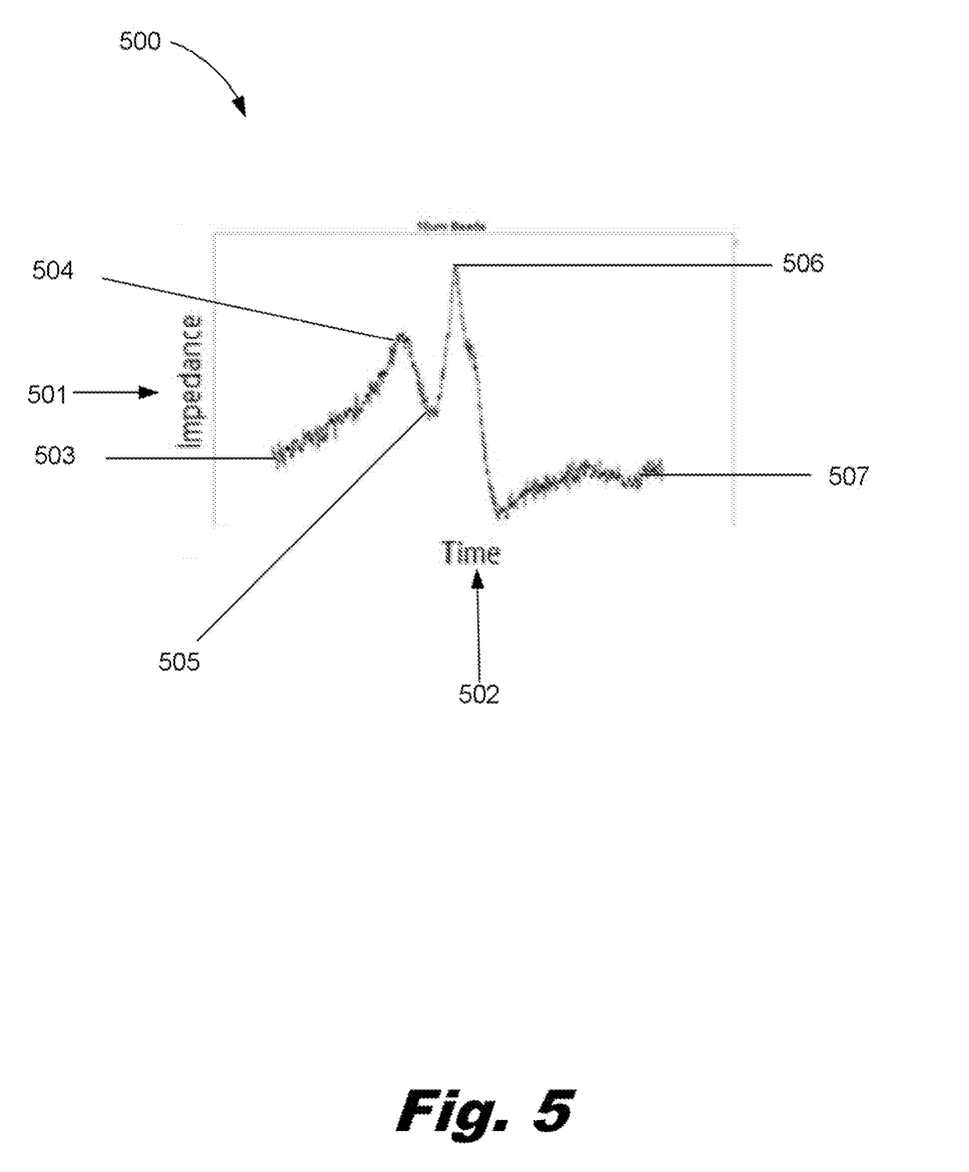
FIG. 5 is a chart of varying impedance as may be observed by a sensor of the apparatus of FIG. 1, according to one example of the principles described herein.

FIG. 5 represents a graph (500) of a measurement of impedance (501) over time (502) by a sensor (FIG. 1, 105). The vertical axis (501) represents increasing impedance on a linear scale. The horizontal axis (502) represents time on a linear scale. A point further in the positive direction of the vertical axis (501) from the horizontal axis (502) represents a measurement of greater impedance. A point further along the horizontal axis (502) that is further away from the vertical axis (501) represents a measurement that is later in time.

The measurement of impedance starts at an initial measurement (503), indicating a relatively low amount of impedance. As a cell (FIG. 4, 402) passes through the electrical field (FIG. 4, 401) it may create a varied electrical field (FIG. 4, 401a). The varied electrical field (FIG. 4, 401a) may be detected by an increase in the impedance measurement to a relatively high impedance (504) (i.e., relative impedance high) with respect to the initial measurement (503).

The impedance measurement may drop to a relatively low impedance (505) (i.e., relative impedance low) with respect to the initial measurement (503) due to a number of factors. The relatively low impedance (505) may be caused by a variation in the shape of the cell (FIG. 4, 402), by where within the electrical field (FIG. 4, 401) the cell (FIG. 4, 402) is, by variations in the solution flow (FIG. 3, 305), by different types of cells passing the sensor (FIG. 1, 105), by multiple cells (FIG. 4, 402) passing the sensor (FIG. 1, 105) and a single cell leaving the measurement area of the sensor (FIG. 1, 105), or combinations thereof.

The impedance measurement may increase to an absolute maximum impedance (506) (i.e., absolute impedance maximum). This absolute maximum impedance (506) may be caused by a cell (FIG. 4, 402) passing a sensor (FIG. 1, 105). The presence of the cell (FIG. 4, 402) may then be processed by the sensor or by the computer device connected by the computer port (FIG. 1, 106). After the cell (FIG. 4, 402) passes the sensor (FIG. 1, 105), the level of impedance measured by the sensing electrode (FIG. 4, 404) may return to a relatively steady state level (507).

While a cell (FIG. 4, 402) may create an absolute maximum impedance (506), a different cell (FIG. 4, 402) may decrease the impedance measured, and create an absolute maximum impedance (506). Another example of a sensor (FIG. 1, 105) may measure the absolute minimum impedance (i.e., absolute impedance minimum) rather than the absolute maximum impedance (506).

Figure 6:
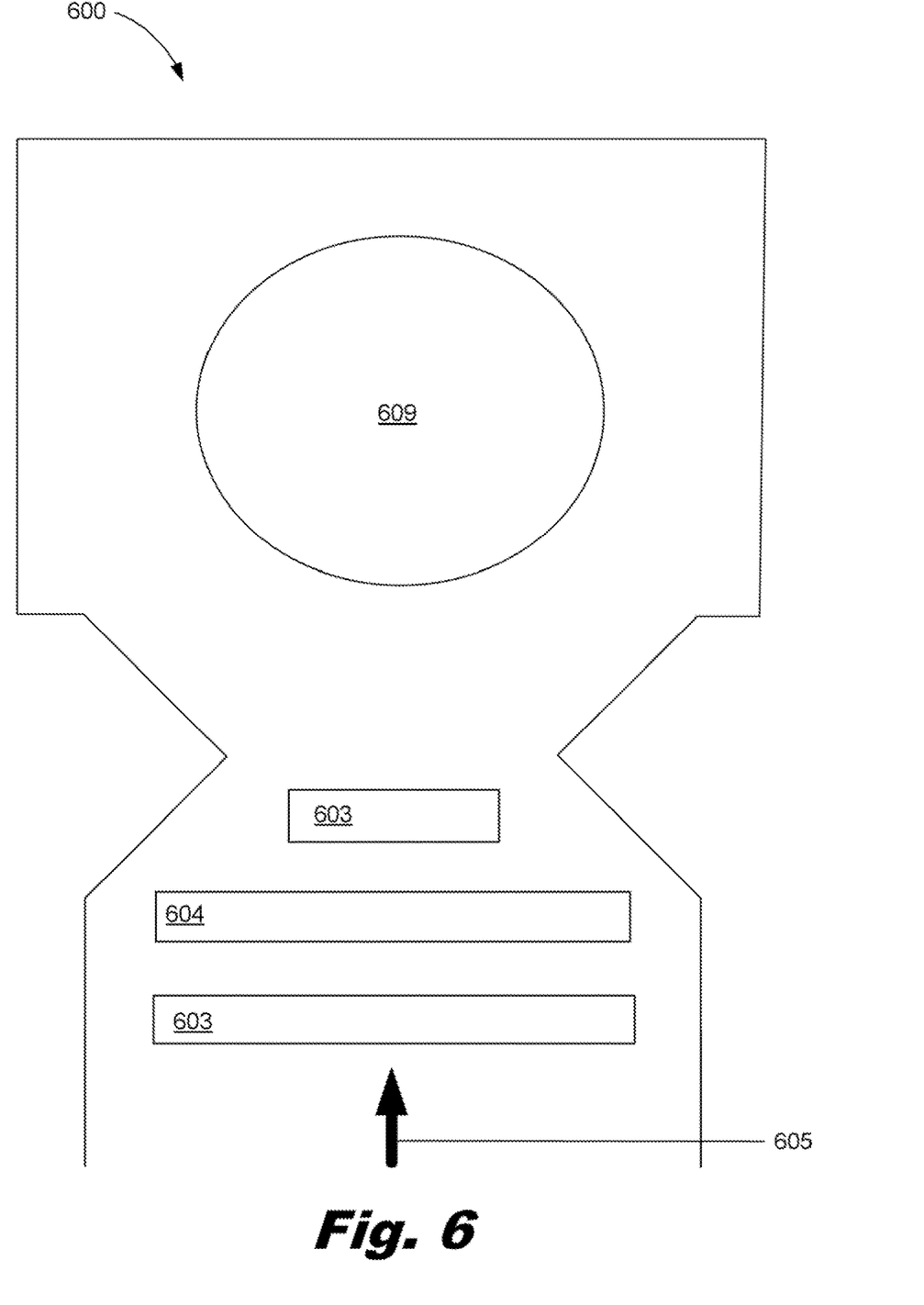
FIG. 6 is a block diagram of a sensor, according to one example of the principles described herein.

FIG. 6 represents an example of a sensor (600) used to measure impedance on a diagnostic cassette (FIG. 1, 100). The sensor (600) may include a pump (609) to create suction to draw the solution flow (605) across a sensing electrode (604) and grounded electrodes (603). As the solution flow (605) passes the sensing electrode (604) it may create variations in the electrical field (FIG. 4, 401) that may be detected.

The pump (600) may be a device such as, for example, a thermal inkjet pump which creates a vacuum drawing the solution past the sensing electrode (604) and grounded electrodes (603). The movement of cells (FIG. 4, 402) in the solution being drawn past the sensing electrode (604) may create a varied electric field (FIG. 4, 401a). By measuring the variation in the varied electric field (FIG. 4, 401a), properties of the cell (FIG. 4, 402) are be calculated by the sensor (FIG. 1, 105). Sensors may be placed at various points along the channel (FIG. 3, 306) to measure attributes of cells (FIG. 4, 402) in the solution.

Figure 7:
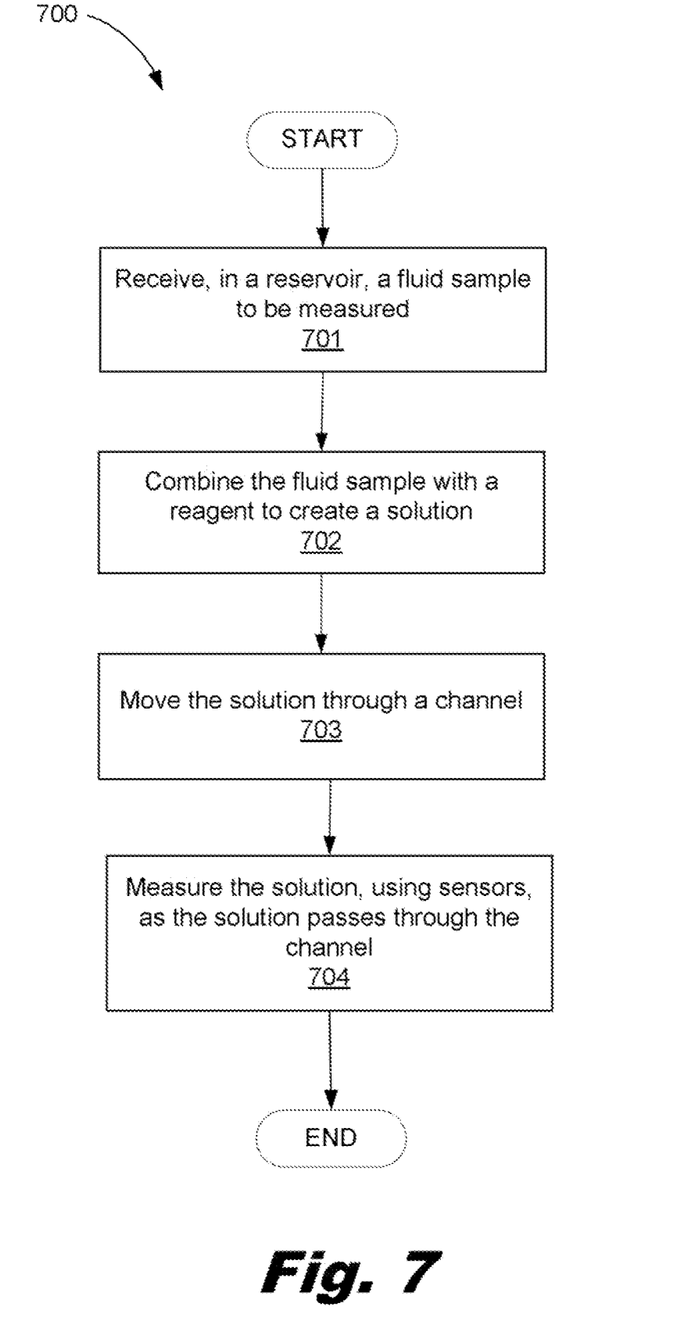
FIG. 7 is a flow chart of a method for measuring a sample, according to one example of the principles described herein.

FIG. 7 represents a method (700) for measuring microfluidic samples. The method may include receiving (block 701), in a reservoir, a fluid sample to be measured. The method (700) may include combining (block 702) the fluid sample with a reagent to create a solution. The method (700) may include moving (block 703) the solution through a channel. As the solution moves (block 703) through the channel, it is measured (block 704) using a number of sensors.

Receiving (block 701), in a reservoir, a fluid sample to be measured may include placing a portion of a fluid sample directly into the reservoir. A fluid sample may be obtained and received (block 701) into by the device using a lance or needle to draw a small amount of fluid from a subject.

Combining (block 702) the fluid sample with a reagent to create a solution may occur in a device such as a diagnostic cassette (FIG. 1, 100). The reagent may be placed in the reservoir receiving the fluid sample either before or after the fluid sample is received. The reagent may be combined (block 702) with the fluid sample to create a solution prior to receiving the fluid sample. The reagent may be combined with the fluid sample as part of a process of moving (block 703) the fluid sample through a channel.

Moving (block 703) the solution through a channel may be achieved by using a pump at one end of or within the channel to create suction to draw the solution toward that end of the channel. Moving (block 703) the solution may also be achieved by placing a pump at one end of or within the channel to create pressure, moving the solution away from that end of the channel.

The channel may be used to control the flow of the solution. The control may allow for a restricted amount of solution to pass a sensor. The control may also allow for greater mixing between the fluid sample and reagent, creating more diffusion between the particles in the solution. The control may also create a delay between the mixing of the fluid sample and the reagent to allow time for reactions between the substances to occur.

As the solution is moving (block 703) through the channel, the diagnostic cassette (100) measures (block 704) the solution, using the sensors, to detect attributes of the solution. The measuring (block 704) may occur with a single sensor, or with multiple sensors. The sensors may be placed serially, or may be placed in parallel. Sensors may be redundant, allowing for repeated measurements of the same portion of the solution.

Figure 8:
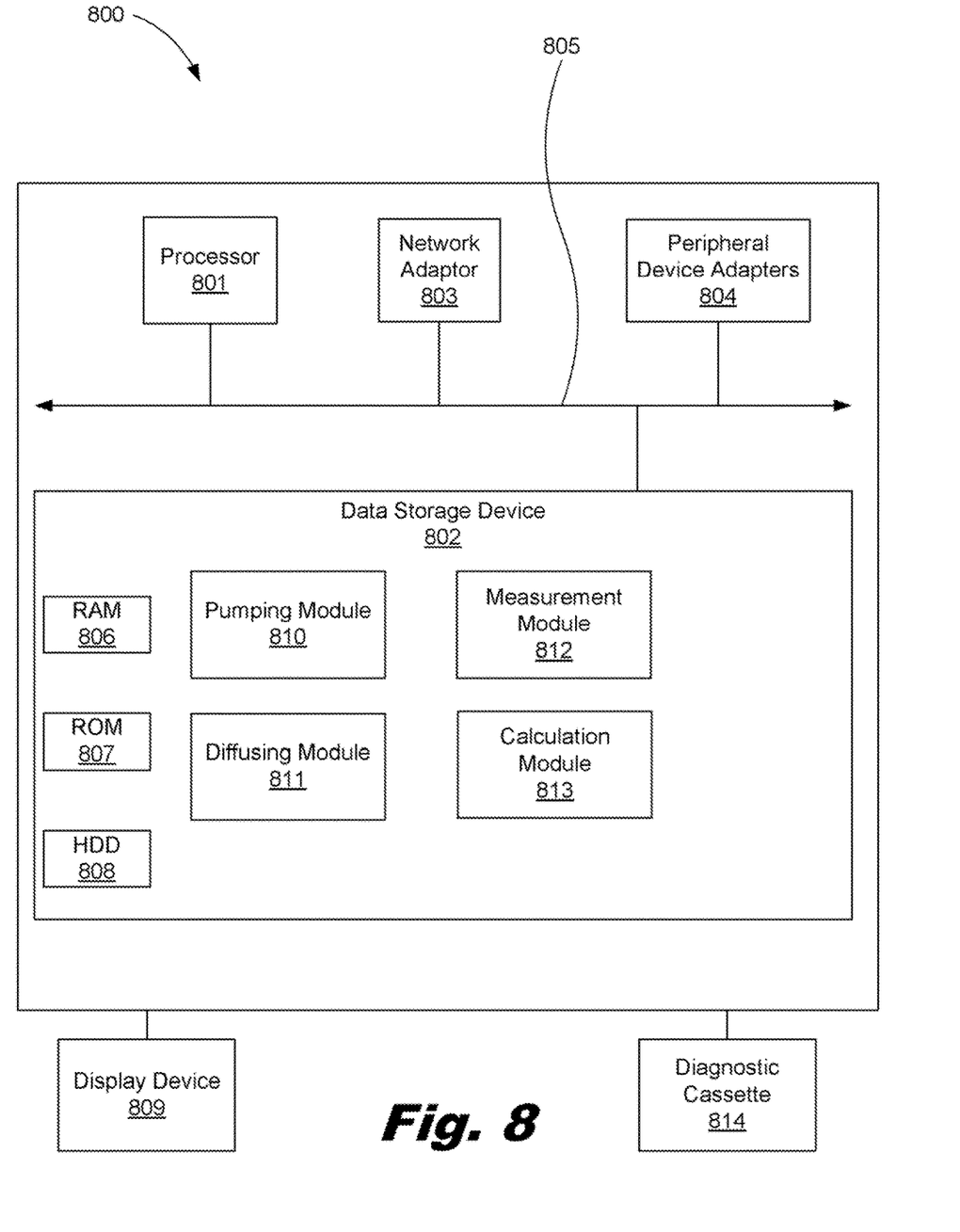
FIG. 8 is a diagram of a computer device for measuring a sample, according to one example of the principles described herein.

FIG. 8 represents a computing device for measuring parameters of a fluid sample according to one example of the principles described herein. The computing device (800) for measuring parameters of fluid samples may be implemented in an electronic device. Examples of electronic devices include servers, desktop computers, laptop computers, personal digital assistants (PDAs), mobile devices, smartphones, gaming systems, and tablets, among other electronic devices.

The computing device (800) may be utilized in any data-processing scenario, including stand-alone hardware, mobile applications, a computing network, or combinations thereof. Further, the computer (800) may be used in a computing network, a public cloud network, a private cloud network, a hybrid cloud network, other forms of networks, or combinations thereof. In one example, the methods provided by the computing device (800) are provided as a service over a network by, for example, a third party. In this example, the service may comprise, for example, the following: a Software as a Service (SaaS) hosting a number of applications; a Platform as a Service (PaaS) hosting a computing platform comprising, for example, operating systems, hardware, and storage, among others; an Infrastructure as a Service (IaaS) hosting equipment such as, for example, servers, storage components, network, and components, among others; application program interface (API) as a service (APIaaS), other forms of network services, or combinations thereof. The present systems may be implemented on one or multiple hardware platforms, in which the modules in the system can be executed on one or across multiple platforms. Such modules can run on various forms of cloud technologies and hybrid cloud technologies or offered as a SaaS (Software as a service) that can be implemented on or off the cloud. In another example, the methods provided by the computing device (800) are executed by a local administrator.

To achieve its desired functionality, the computing device (800) comprises various hardware components. Among these hardware components may be a number of processors (801), a number of data storage devices (802), a number of peripheral device adapters (804), and a number of network adapters (803). These hardware components may be interconnected through the use of a number of busses and/or network connections. In one example, the processor (801), data storage device (802), peripheral device adapters (804), and a network adapter (803) may be communicatively coupled via a bus (805).

The processor (801) may include the hardware architecture to retrieve executable code from the data storage device (802) and execute the executable code. The executable code may, when executed by the processor (801), cause the processor (801) to implement at least the functionality of processing data obtained from the diagnostic cassette (814), according to the methods of the present specification described herein. In the course of executing code, the processor (801) may receive input from, and provide output to, a number of the remaining hardware units.

The data storage device (802) may store data, such as executable program code, that is executed by the processor (801) or other processing device. As will be discussed, the data storage device (802) may specifically store computer code representing a number of applications that the processor (801) executes to implement at least the functionality described herein.

The data storage device (802) may include various types of memory modules, including volatile and nonvolatile memory. For example, the data storage device (802) of the present example includes Random Access Memory (RAM) (806), Read Only Memory (ROM) (807), and Hard Disk Drive (HDD) memory (808). Many other types of memory may also be utilized, and the present specification contemplates the use of many varying type(s) of memory in the data storage device (802) as may suit a particular application of the principles described herein. In certain examples, different types of memory in the data storage device (802) may be used for different data storage needs. For example, in certain examples the processor (801) may boot from Read Only Memory (ROM) (807), maintain nonvolatile storage in the Hard Disk Drive (HDD) memory (808), and execute program code stored in Random Access Memory (RAM) (806).

Generally, the data storage device (802) may comprise a computer readable medium, a computer readable storage medium, or a non-transitory computer readable medium, among others. For example, the data storage device (802) may be, but is not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store computer usable program code for use by or in connection with an instruction execution system, apparatus, or device. In another example, a computer readable storage medium may be any non-transitory medium that can contain, or store a program for use by or in connection with an instruction execution system, apparatus, or device.

The hardware adapters (803, 804) in the computing device (800) enable the processor (801) to interface with various other hardware elements, external and internal to the computing device (800). For example, the peripheral device adapters (804) may provide an interface to input/output devices, such as, for example, a display device (809), a mouse, a keyboard or the diagnostic cassette (814). The peripheral device adapters (803) may also provide access to other external devices, such as an external storage device, a number of network devices such as, for example, servers, switches, and routers, client devices, other types of computing devices, and combinations thereof.

The display device (809) may be provided to allow a user of the computing device (800) to interact with and implement the functionality of the computing device (800). The peripheral device adapters (804) may also create an interface between the processor (801) and the display device (809), a printer, or other media output devices. The network adapter (803) may provide an interface to other computing devices within, for example, a network, thereby enabling the transmission of data between the computing device (800) and other devices located within the network.

The computing device (800) may, when executed by the processor (801), display the number of graphical user interfaces (GUIs) on the display device (809) associated with the executable program code, representing the number of applications stored on the data storage device (802). The GUIs may include aspects of the executable code, including measurements taken of properties of a fluid sample. The GUIs may display, for example, a count of a particular type of cell carrying a particular attribute. Additionally, via making a number of interactive gestures on the GUIs of the display device (809), a user may display additional information regarding properties of other particles in the fluid sample. Examples of display devices (809) include a computer screen, a laptop screen, a mobile device screen, a personal digital assistant (PDA) screen, and a tablet screen, among other display devices (809). Examples of the GUIs displayed on the display device (809) will be described in more detail below.

The computing device (800) further comprises a number of modules used in the implementation of measuring properties of a fluid sample. The various modules within the computing device (800) comprise executable program code that may be executed separately. In this example, the various modules may be stored as separate computer program products. In another example, the various modules within the computing device (800) may be combined within a number of computer program products; each computer program product comprising a number of the modules.

The computing device (800) may include a pumping module (810) to, when executed by the processor (801), allow a fluid sample to be circulated through channels on a diagnostic device. The pumping module (810) causes a solution of a fluid sample and a reagent to pass through channels on the diagnostic cassette (814). By controlling the amount of pressure created by the pumping, a time can be established to allow for diffusion and reaction between a fluid sample and a reagent.

The computing device (800) may include a diffusing module (811) which, when executed by the processor (801), diffuses a reagent and a fluid sample. Diffusion may occur by controlling a pump to create movement of particles in the solution of the fluid sample and the reagent. The diffusion may further be facilitated by physical characteristics of the channels through which the solution is passing.

The computing device (800) may include a measurement module (812) which, when executed by the processor (801), measures properties of particles in the solution of the fluid sample and the reagent. The measurement may involve a single sensor or multiple sensors. The sensors may measure a single attribute or multiple attributes of the solution.

Based on measurements within the measurement module (812), the calculation module (813) may perform calculations on the data and present the data to a user through a display device (809). The calculation may involve processes such as adding the measurement of a number of sensors, comparing the measurement of a number of sensors, averaging the measurement of a number of sensors, or any of a number of numerical analyses may be taken to present a number to a user that may be understood and acted upon.

Aspects of the present system and method are described herein with reference to flowchart illustrations and/or block diagrams of methods, apparatus (systems) and computer program products according to examples of the principles described herein. Each block of the flowchart illustrations and block diagrams, and combinations of blocks in the flowchart illustrations and block diagrams, may be implemented by computer usable program code. The computer usable program code may be provided to a processor of a general purpose computer, special purpose computer, or other programmable data processing apparatus to produce a machine, such that the computer usable program code, when executed via, for example, the processor (801) of the computing device (800) or other programmable data processing apparatus, implement the functions or acts specified in the flowchart and/or block diagram block or blocks. In one example, the computer usable program code may be embodied within a computer readable storage medium; the computer readable storage medium being part of the computer program product. In one example, the computer readable storage medium is a non-transitory computer readable medium.

The preceding description has been presented to illustrate and describe examples of the principles described. This description is not intended to be exhaustive or to limit these principles to any precise form disclosed. Many modifications and variations are possible in light of the above teaching.

What is claimed is:

1. A diagnostic cassette, comprising: a substrate; a reservoir defined within the substrate to receive a fluid sample for processing by the diagnostic cassette; a reagent to react with the fluid sample deposited in the reservoir to form a solution to enable processing of the fluid sample by the diagnostic cassette; a channel to direct the solution, the channel comprising a number of microstructures to impede flow of the solution through the channel, the number of microstructures corresponding to an amount of time needed for a predetermined degree of reaction between the sample and reagent; a sensor to measure a number of parameters of the solution passing through the channel, wherein the sensor detects a type of cell in the solution by measuring impedance and detecting an impedance signature of a type of cell as modified by reaction with the reagent in the solution; and a port on the substrate to electrically connect the sensor with a computing device.

2. A diagnostic cassette, comprising: a substrate; a reservoir defined within the substrate to receive a fluid sample for processing by the diagnostic cassette; a reagent to react with the fluid sample deposited in the reservoir to form a solution to enable processing of the fluid sample by the diagnostic cassette; a channel to direct the solution, the channel comprising a number of microstructures to impede flow of the solution through the channel, the number of microstructures corresponding to an amount of time needed for a predetermined degree of reaction between the sample and reagent; a sensor to measure a number of parameters of the solution passing through the channel, wherein the sensor comprises a series of sensors to sort cells in the solution based on multiple attributes; and a port on the substrate to electrically connect the sensor with a computing device.

* * * * *